(12) United States Patent
Pizzi et al.

(10) Patent No.: US 10,639,237 B2
(45) Date of Patent: May 5, 2020

(54) ASEPTIC CONNECTORS WITH INTEGRATED WIRELESS CONNECTIVITY

(71) Applicant: GE HEALTHCARE BIO-SCIENCES CORP., Marlborough, MA (US)

(72) Inventors: Vincent Francis Pizzi, Marlborough, MA (US); Christopher Dakin McCoy, Marlborough, MA (US)

(73) Assignee: GE HEALTHCARE BIO-SCIENCES CORP., Marlborough, MA (US)

( * ) Notice: Subject to any disclaimer, the term of this patent is extended or adjusted under 35 U.S.C. 154(b) by 117 days.

(21) Appl. No.: 16/130,685

(22) Filed: Sep. 13, 2018

(65) Prior Publication Data

US 2020/0085689 A1    Mar. 19, 2020

(51) Int. Cl.
| | | |
|---|---|---|
| *A61J 1/10* | (2006.01) | |
| *A61J 1/14* | (2006.01) | |
| *A61M 39/18* | (2006.01) | |
| *A61M 39/14* | (2006.01) | |

(52) U.S. Cl.
CPC .............. *A61J 1/1475* (2013.01); *A61J 1/10* (2013.01); *A61M 39/14* (2013.01); *A61M 39/18* (2013.01)

(58) Field of Classification Search
CPC .................................. A61J 1/10; A61J 1/1475
USPC ....................................................... 73/866.5
See application file for complete search history.

(56) References Cited

U.S. PATENT DOCUMENTS

| | | | |
|---|---|---|---|
| 8,587,410 B2 | 11/2013 | Potyrailo et al. | |
| 9,927,052 B1* | 3/2018 | Robillard | F16L 23/18 |
| 2012/0001768 A1* | 1/2012 | Radosavljevic | H04Q 9/00 340/870.03 |
| 2017/0089496 A1* | 3/2017 | Lennon | G01M 5/0083 |

FOREIGN PATENT DOCUMENTS

WO    2017/053712 A1    3/2017

OTHER PUBLICATIONS

PCT International Search Report and Written Opinion for PCT Application No. PCT/EP2019/073209 dated Dec. 12, 2019 (14 pages).

* cited by examiner

*Primary Examiner* — Jamel E Williams
(74) *Attorney, Agent, or Firm* — Eversheds Sutherland (US) LLP (57) ABSTRACT

The present disclosure relates to aseptic connectors with integrated wireless connectivity. For example, an example system may include a removable clamp configured to secure a first portion of an aseptic connector to a second portion of the aseptic connector. The removable clamp may include a housing, a controller disposed within the housing, a rechargeable battery disposed within the housing, a wireless radio disposed within the housing, and a sensor plug receptacle configured to receive a sensor plug coupled to a sensor of the aseptic connector. The controller may be configured to determine a sensor output of the sensor and to transmit the output using the wireless radio.

20 Claims, 7 Drawing Sheets

ASEPTIC CONNECTORS WITH INTEGRATED WIRELESS CONNECTIVITY

TECHNICAL FIELD

The present disclosure relates to fluid connectors, and, more specifically, aseptic connectors with integrated wireless connectivity.

BACKGROUND

In bioprocess environments, a series of actions or steps are taken in a prescribed sequence to develop and/or purify one or more desired products. These series of actions or steps is known as bioprocess operation in the bioprocess environment. However, a proper control and monitoring of the bioprocess operation may be required to develop these desired products.

Many bioprocess systems use equipment to monitor and control the bioprocess operation. In one example, the equipment includes filters, circuits, disposable components, and the like. These components may have tubing connections between them to convey fluid from one component to another. Wired sensors may be disposed on the components and/or the tubing connections to measure parameters in the bioprocess environment. Some of these parameters include temperature, pressure, a potential of hydrogen (pH), and dissolved oxygen (DO) in the fluid. Such sensors may be connected to an external reader using wires to track the measured parameters. Due to wired connections, there it may be challenging to position certain sensors at desired locations in the bioprocess environment. Accordingly, there is a need for an improved system and method to monitor and control the bioprocess in the bioprocess environment.

SUMMARY

According to an embodiment of the disclosure, a system may include a removable clamp configured to secure a first portion of an aseptic connector to a second portion of the aseptic connector. The removable clamp may include a housing, a controller disposed within the housing, a rechargeable battery disposed within the housing, a wireless radio disposed within the housing, and a sensor plug receptacle configured to receive a sensor plug coupled to a sensor of the aseptic connector. The controller may be configured to determine a sensor output of the sensor and to transmit the output using the wireless radio. The system may include the aseptic connector, where second portion of the aseptic connector is a connector body, and where the sensor is disposed within the connector body. The first portion of the aseptic connector may be an insert portion, and a fluid may flow through the connector body to the insert portion. The sensor may be a single use integrated sensor. The sensor may be removably coupled to the connector body. The sensor plug may be configured to detach from the sensor plug receptacle. The removable clamp may include a pivotable arm that is configured to pivot with respect to the housing. The removable clamp may include a rotatable screw to secure the pivotable arm to the housing. The rechargeable battery may be configured to be inductively charged. The sensor may be one or more of: a pressure transducer, a temperature sensor, a flow meter sensor, or a conductivity sensor. The rechargeable battery may be configured to power the sensor, the controller, and the wireless radio. The wireless radio may be a Bluetooth radio or a ZigBee radio. The sensor may be a first sensor, and the system may include a second sensor at the aseptic connector. The controller may be configured to transmit the output over a local area network.

According to another embodiment, a method may include placing a first portion of an aseptic connector adjacent to a second portion of the aseptic connector, where the aseptic connector comprises a removable sensor coupled to the second portion, clamping the first portion to the second portion using a removable clamp, where the removable claim comprises a housing, a rechargeable battery disposed within the housing, and a wireless radio disposed within the housing, determining a sensor output of the removable sensor, and transmitting the sensor output using the wireless radio.

According to another embodiment, an aseptic connector clamp system may include an aseptic connector that includes an insert portion, a connector body, and an integrated sensor coupled to the connector body, the integrated sensor coupled to a sensor plug. The aseptic connector clamp system may include a removable clamp configured to secure the insert portion to the connector body, the removable clamp including a housing, a controller disposed within the housing, a rechargeable battery disposed within the housing, a wireless radio disposed within the housing, and a sensor plug receptacle configured to receive the sensor plug. The controller may be configured to determine a sensor output of the integrated sensor and to transmit the output using the wireless radio. The rechargeable battery may be configured to be inductively charged. The wireless radio may be a Bluetooth radio or a ZigBee radio. The aseptic connector may be disposable.

DETAILED DESCRIPTION

As will be described in detail hereinafter, various embodiments of systems and methods for using aseptic connectors with integrated wireless connectivity are presented. In some embodiments, the systems and methods presented herein employ sensors and wireless data transmission to monitor and/or control a bioprocess operation in a bioprocess environment. Further, the monitoring of sensor measurements and/or output may be performed using wireless data transmissions, thereby reducing an amount of wires at a system and decreasing clutter. Some embodiments may include reusable clamps that secure connectors together and that house electronic components for wireless data transmission. As a result, disposable aseptic connectors and/or sensor systems may be used with reusable clamps that enable wireless connectivity functionality.

In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable.

Unless defined otherwise, technical and scientific terms used herein have the same meaning as is commonly understood by one of ordinary skill in the art to which this specification belongs. The terms "first", "second", and the like, as used herein do not denote any order, quantity, or importance, but rather are used to distinguish one element from another. The use of terms "including," "comprising" or "having" and variations thereof herein are meant to encompass the items listed thereafter and equivalents thereof as well as additional items. The terms "connected" and "coupled" are not restricted to physical or mechanical connections or couplings and can include electrical connections or couplings, whether direct or indirect. Furthermore, terms "circuit," "circuitry," "controller," and "control unit" may include either a single component or a plurality of components, which are either active and/or passive and are connected or otherwise coupled together to provide the described function. In addition, the term operationally or operatively coupled as used herein includes wired coupling, wireless coupling, electrical coupling, magnetic coupling, radio communication, software based communication, or combinations thereof.

Some embodiments of the disclosure include rechargeable devices, such as clamps, to power and/or send wireless signals from single use sensor(s) embedded in aseptic connectors. Accordingly, certain aseptic connector systems may include integrated sensors or other sensing elements and wireless transmission functionality.

Aseptic connectors may be used to flow material, such as fluid, from one location to another. Embodiments of the disclosure include aseptic connector systems that are configured to collect data using one or more, or a plurality of, sensors integrated at an aseptic connector, and to wirelessly transmit the data using a wireless radio. In some instances, certain electronic components, such as a wireless radio, controller, battery, and/or other components may be disposed in a secondary component of the system, such as in a housing of a clamp that secures or couples the aseptic connector together. The clamp may include one or more lithium ion batteries to power, among other components, the embedded or integrated sensor(s) in the aseptic connector, and may be configured to send data from the sensor(s) to another device via a wireless network, such as a local area network (LAN) on which one or more sensor transmitters reside. When the clamp is not in use, the clamp may be inductively recharged on a charging station with other clamps. It should be noted that the clamp, as referred to herein, could be in a different format that still provides power to the integrated sensor(s) and/or transmits data wirelessly.

As a result of embodiments of this disclosure, cluttering of bio-manufacturing production areas with tubing and wires (that pose a potentially confusing and hazardous environment for operators) may be reduced. Some embodiments may reduce an amount of wiring present in a manufacturing area thereby reducing clutter. Furthermore, some embodiments include clamps that can be configured for specific tasks using process automation and/or may be color coded so they are easily identifiable by operators. In addition, bioprocessing entities using sterile sensing technology may be limited to predetermined points in the workflow. If the sensing point is predetermined, certain embodiments include aseptic connectors with sensing elements that may be pre-assembled prior to sterilization. Embodiments may include a clamp used to complete the secure seal between two portions of an aseptic connector, and may be the interface for excitation and data transmission.

The disclosure will now be described more closely in association with the accompanying drawings and some non-limiting examples.

Figure 1:
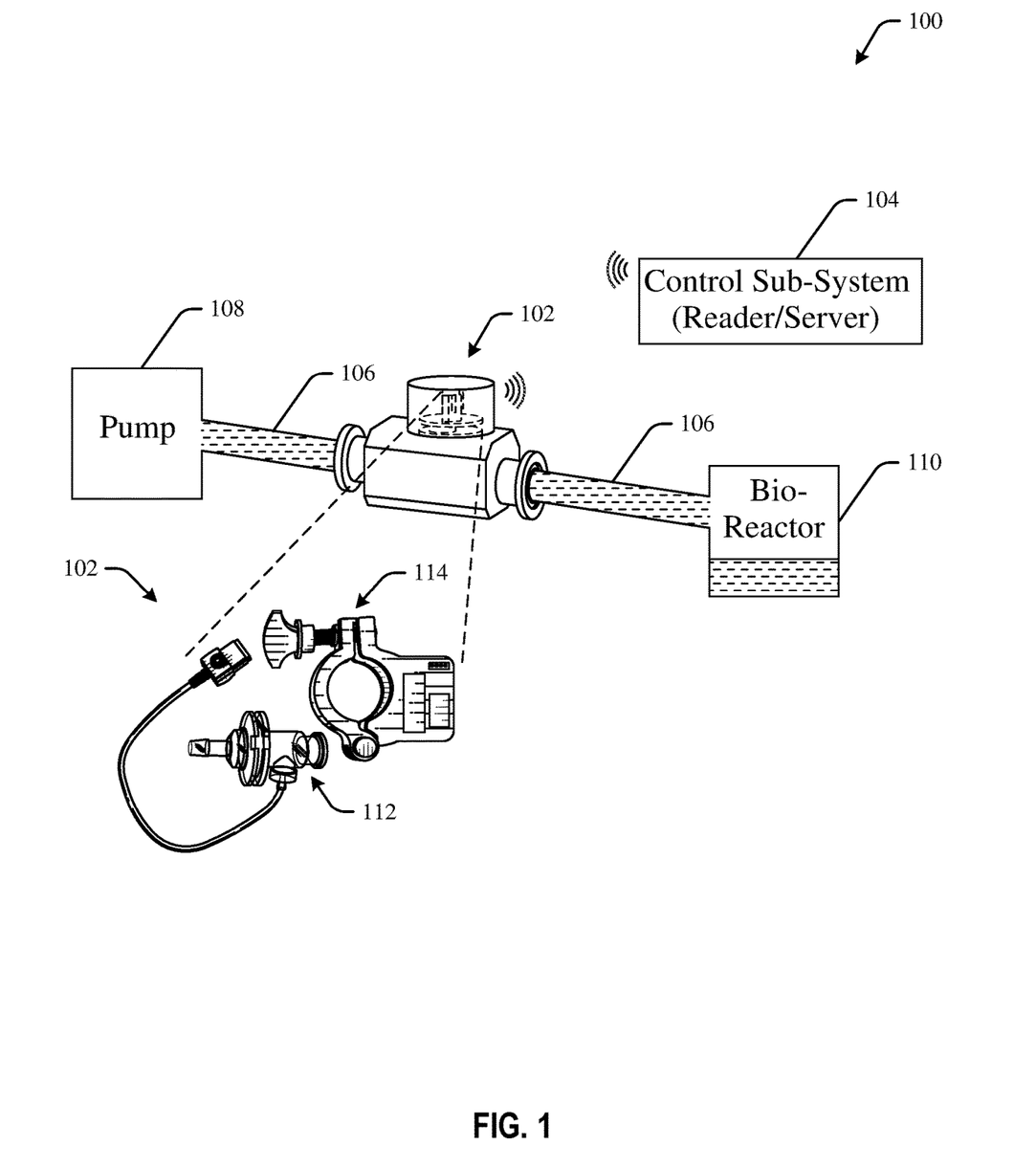
FIG. 1 is a schematic drawing of an example aseptic connector system use case in accordance with one or more embodiments of the disclosure.

FIG. 1 is a schematic drawing of an example aseptic connector system use case 100 in accordance with one or more embodiments of the disclosure. In certain embodiments, the bioprocess environment may include biodevices, such as bioreactors, cell banking units, filters, cell harvesting units, chromatography units, circuits, wave rockers, protein concentration units, sterile filtration units, virus removal units, product holding units, buffer preparation units, media preparation units, buffer holding units, media holding units, pumps, flexible cell culture bags, mixers, tanks, safety units, other disposable components and the like. Some of these devices may be connected to each other with tubes, clamps, and/or smart switches that aid in conveying and controlling fluid from one device to another device.

Bioprocess operation may performed using one or more of these devices in the bioprocess environment to develop and/or purify the desired products. It may be noted that bioprocess operation is referred to as a series of actions or steps that are taken in a prescribed sequence on living cells, organisms, or their molecular components in the fluid to develop the desired products in the bioprocess environment. Some of the bioprocess operations may include processing of genetically engineered organisms or cells to obtain the desired products.

Bioprocessing components may include a sensing subsystem 102 and a control subsystem 104. A portion of the, or the entire, sensing subsystem 102 may be single-use. For example, a sensing element in the sensing subsystem that is contact with a fluid may be disposable or reusable after a cycle of bioprocess operation. It can suitably be pre-sterilized, e.g. by radiation sterilization. After disposing the sensing-subsystem, a new sensing element may be electrically coupled with existing components for another cycle of bioprocess operation. The cycle of bioprocess operation may be referred to as a time taken to complete a series of actions or steps in a prescribed sequence to develop the desired product. The term "single-use" is referred as the usage of the device/component for only one cycle of bioprocess operation. After one cycle of bioprocess operation, the device/component may be disposed.

The sensing subsystem 102 may be configured to measure one or more parameters in the bioprocess operation. Some of the parameters include pressure of the fluid employed for one or more applications in the bioprocess environment, electrical conductivity of the fluid, a biomass in the fluid, a dissolved gas level in the fluid, temperature of the fluid, glucose flow in the fluid, a viable cell density in the fluid, a flow rate of the fluid, a level of foam in the fluid, and a potential of hydrogen (pH) level in the fluid. It may be noted that the sensing subsystem 102 may be positioned at any desired location, such as on the bioreactors, the filtration unit, the circuits, the disposable components, the flexible cell culture bags, the pumps, and the connecting tubes in the bioprocess environment.

In some embodiments, the sensing subsystem 102 may be operatively coupled to connecting tubes 106 that are positioned between one or more pumps 108 and one or more bioreactors 110. Sensing subsystems 102 may be used as key building blocks of a flexible flow path. In the embodiment depicted in FIG. 1, the sensing subsystem 102 may be configured to measure the parameters of the fluid that flows from the pump 108 to the bioreactor 110 via the connecting tubes 106. However, the sensing subsystem 102 may be configured to be disposed in other components of the bioprocess environment as well, for example, in the bioreactor itself. In such embodiments, the sensing subsystem 102 may be configured to measure the parameters of the fluid that the sensing subsystem 102 is in contact with. In certain embodiments, the sensing subsystem 102 may include a single-use wired or wireless sensor.

The pump 108 may be coupled to the bioreactor 110 via the tubes 106 and/or tubing chambers. In one example, the tubes 208 are flexible and disposable plastic tubes. Further, the pump 108 may be configured to supply fluid to the bioreactor 110 where the bioprocess operations, such as cell cultivation, takes place. In one example, the bioreactor 110 may include a flexible cell culture bag that aids in cultivating the cells in the fluid.

The sensing subsystem 102 may be at least partially disposed in the tubes 106 and may be configured to measure one or more parameters of the fluid conveyed from the pump 108 to the bioreactor 110. In one example, a portion of the sensing subsystem 102 is in contact with the fluid that is flowing through the tubes 106 to measure the parameters of the fluid. For example, the sensing subsystem 102 may include a sensing element and a signal processor. The sensing element may be a sensor that is in contact with the fluid in the tubes 106 to sense analog data corresponding to the parameters of the fluid. The signal processor may be used to process the analog data to generate the parameters of the fluid. More specifically, the signal processor may convert the analog data to digital data that represents the measured parameters of the fluid.

Figure 2:
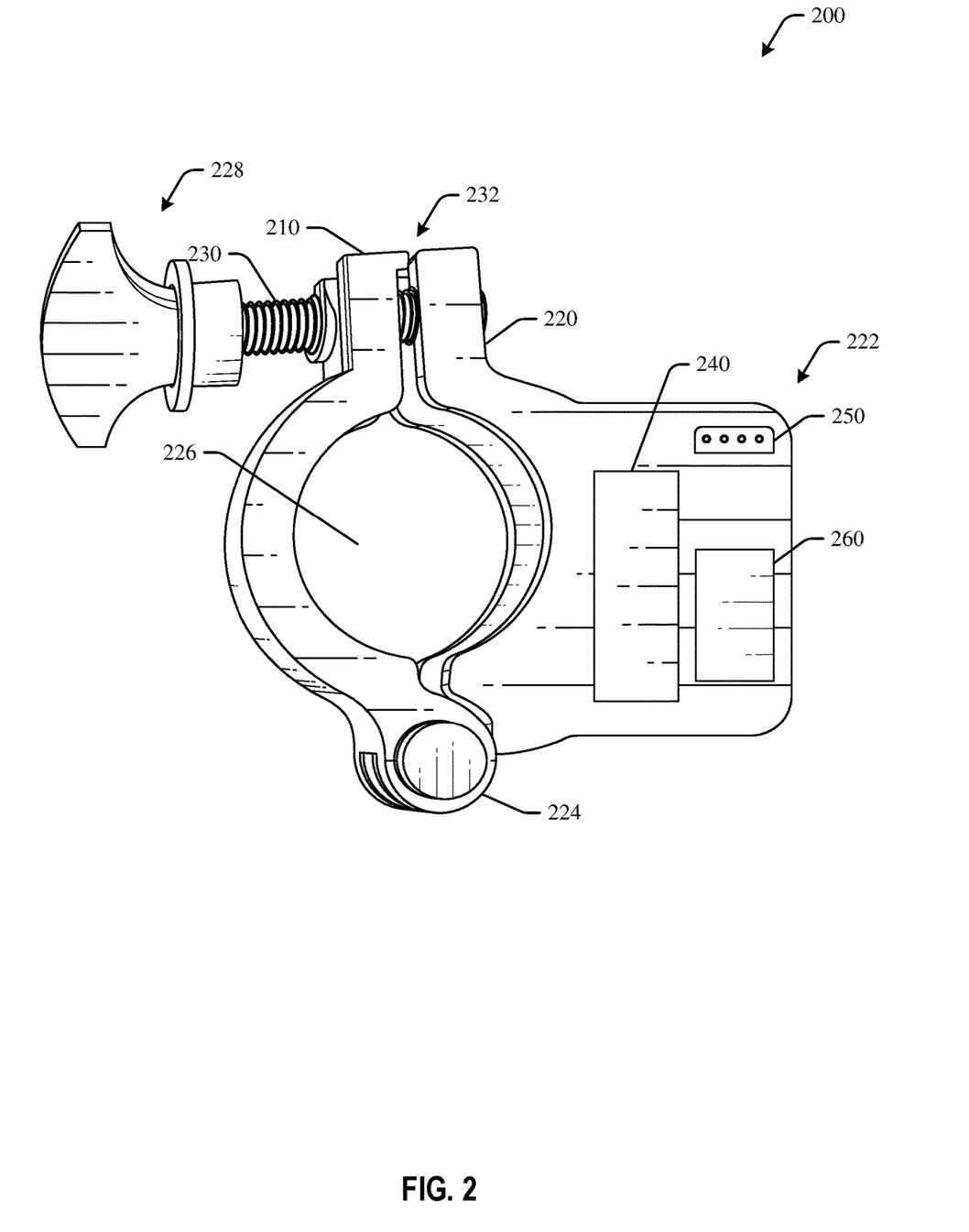
FIG. 2 is a schematic drawing of an example clamp in accordance with one or more embodiments of the disclosure.
Figure 3A:
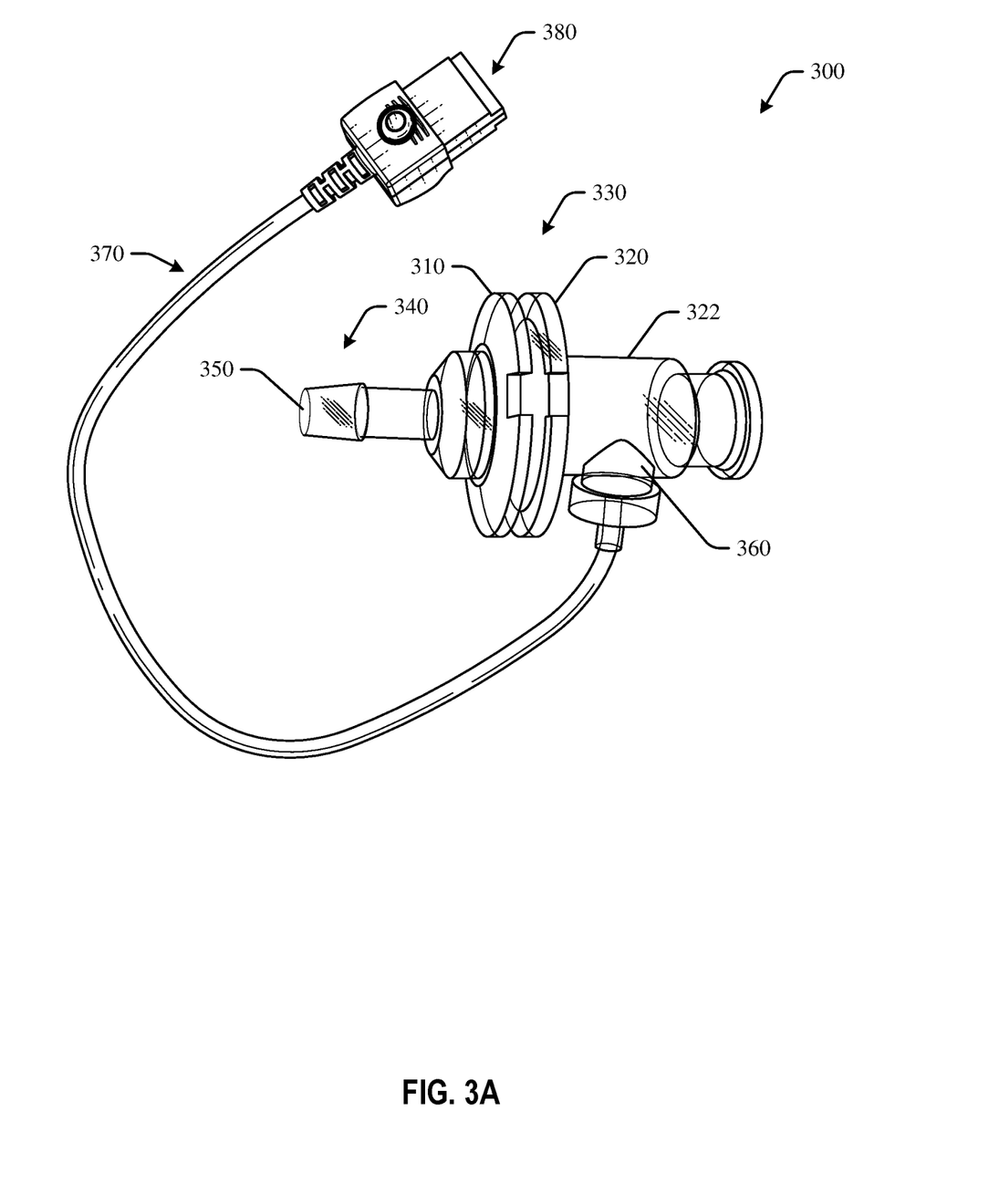
FIG. 3A is a schematic drawing of an example aseptic connector in accordance with one or more embodiments of the disclosure.
Figure 3B:
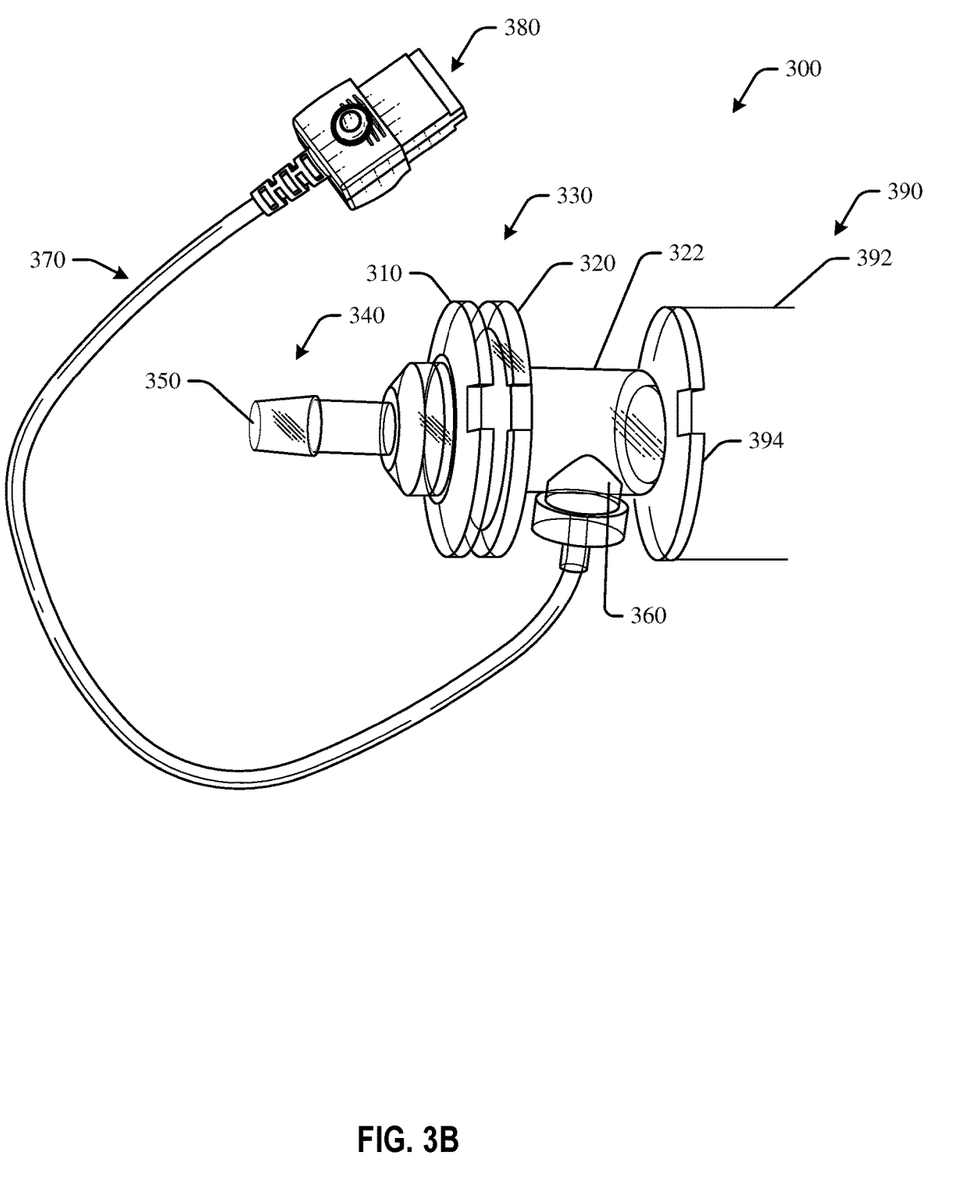
FIG. 3B is a schematic drawing of an example aseptic connector with a spool piece in accordance with one or more embodiments of the disclosure.
Figure 4:
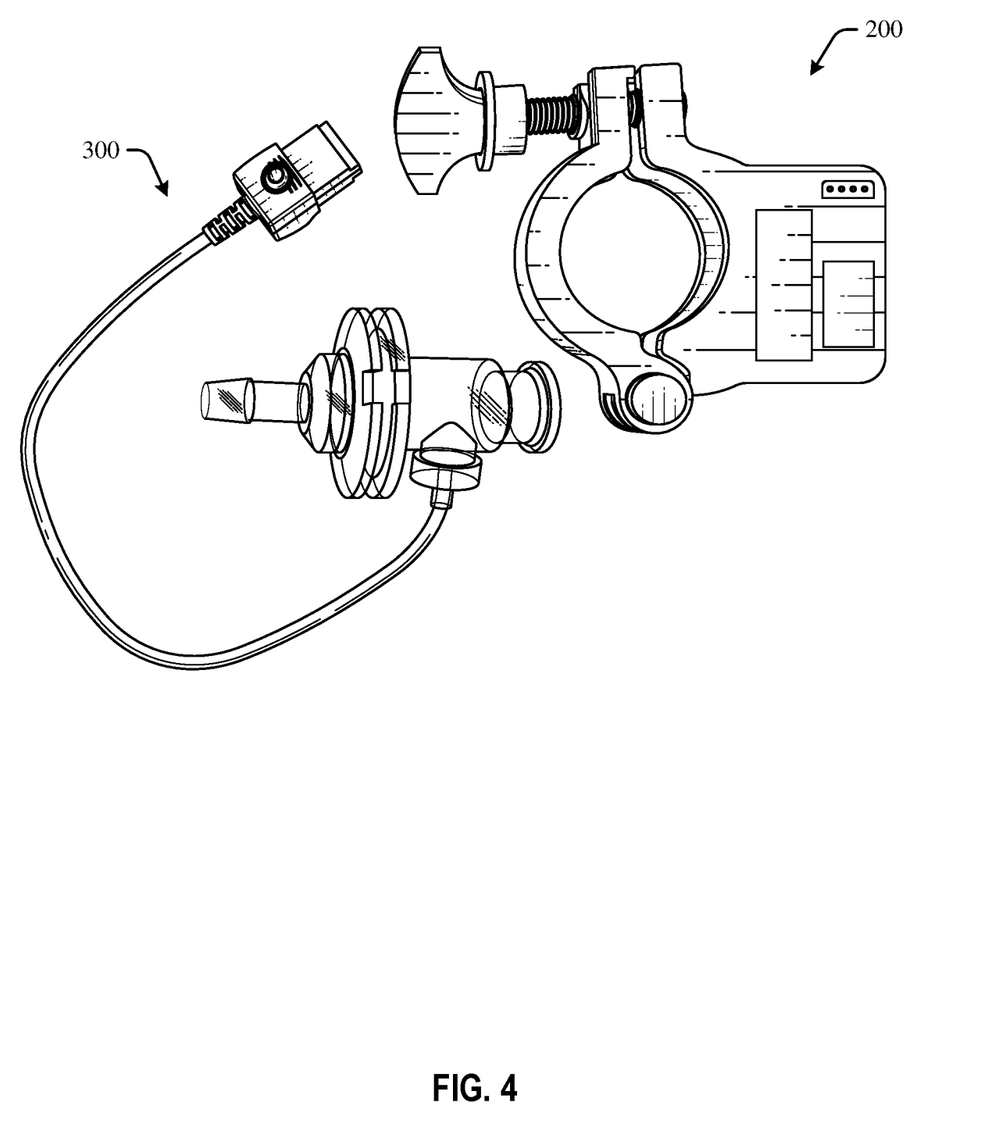
FIG. 4 is a schematic drawing of the clamp of FIG. 2 and the aseptic connector of FIG. 3A in accordance with one or more embodiments of the disclosure.

As illustrated in FIG. 1, the sensing subsystem 102 may include an aseptic connector 112 and a clamp 114. It may be noted that the sensing subsystem 102 may include other components, and is not limited to the components depicted in FIG. 1. FIGS. 2-4 illustrate example embodiments of aseptic connectors and clamps in detail.

The sensing subsystems in accordance with some embodiments of the specification may allow for modular sensors such that the sensor components can be designed and fitted together in variety of configurations. The modular sensor may be referred as a sensing device where one or more internal elements/components of the sensor may be separated or disintegrated from other internal elements/components in the sensor.

The control subsystem 104 may be operationally coupled to the sensing subsystem 102 to receive one or more measured parameters or characteristics (and/or other outputs) of the fluid from the sensing subsystem 102. In one example, the control subsystem 104 may receive one or more sensed signals that represent the measured parameters of the fluid. It may be noted that control subsystem 104 may be coupled to a plurality of sensing subsystems, and is not limited to a single sensing subsystem 102 as depicted in FIG. 1.

In certain embodiments, the control subsystem 104 is in wireless communication with the sensing subsystem 102 to receive the measured parameters of the fluid from the sensing subsystem 102. In one example, the control subsystem 104 may be wirelessly coupled to the sensing subsystem 102 using any wireless communication techniques, such as infrared, short-range radio frequency (RF) communication, Bluetooth, Bluetooth Low Energy (BLE), Wi-Fi, Wi-Max, Global System for Mobile (GSM), General Packet Radio Service (GPRS), Code Division Multiple Access (CDMA), High-Speed Downlink Packet Access (HSDPA), ZigBee, and the like.

The control subsystem 104 may include a first controller and a user interface unit that are electrically coupled to each other. The user interface unit may be referred to as an input-output (I/O) device that is configured to receive data from a user and/or display data to the user. In one embodiment, the user interface unit is configured to receive user-input data. The user-input data may include data indicating an application of the sensing subsystem 102 and/or at least one desired parameter of the fluid in the bioprocess environment. The application of the sensing subsystem 102 may include usage of the sensing subsystem 102 in the biodevices, such as the bioreactors, the filtration units, the chromatography units, the mixers/tanks, and/or the safety units. In certain embodiments, the user may select one or more options from a drop-down menu in the user interface unit. These selected options may be used as the user input data and/or the sensing subsystem data. Further, the user interface unit transmits the user-input data to the first controller.

In a similar manner, the first controller may receive a sensing subsystem data from the sensing subsystem 102. The sensing subsystem data may include data indicating a type of the sensing subsystem 102 and/or other information. In one example, the data indicating the type of the sensing subsystem 102 may be used to identify the sensor(s), such as the pressure sensor, the temperature sensor, the pH sensor, the conductivity sensor, the glucose sensor, the biomass sensor, the cell viability sensor, the oxygen sensor, the carbon-dioxide sensor, the ultraviolet (UV) sensor, the flow sensor, the foam sensor, and/or a different sensor employed in the bioprocess environment. In one embodiment, the first controller may receive the sensing subsystem data from a user via the user interface unit.

The sensing subsystem 102 may be wireles sly coupled to the control subsystem 104 to communicate the measured parameters of the fluid to the control subsystem 104. In one example, the sensing subsystem 102 may transmit one or more signals that represent the measured parameters of the fluid. The control subsystem may also be referred to as a reader. The control subsystem 104 may be disposed external to the sensing subsystems.

FIG. 2 illustrates an example clamp 200 in accordance with one or more embodiments of the disclosure. The clamp 200 may be the same or different than the clamp 114 discussed with respect to FIG. 1. Other embodiments may include clamps with additional or fewer, or different, components. The clamp 200 may be part of a system, such as an aseptic connector clamp system (illustrated in FIG. 4), or may be a standalone component.

FIG. 3A illustrates an example aseptic connector 300 in accordance with one or more embodiments of the disclosure. FIG. 3A will be discussed in conjunction with FIG. 2. The aseptic connector 300 may be the same or different than the aseptic connector 112 discussed with respect to FIG. 1. Other embodiments may include connectors with additional or fewer, or different, components. The aseptic connector 300 may be part of a system, such as an aseptic connector clamp system (illustrated in FIG. 4), or may be a standalone component.

With reference to FIGS. 2-3, the clamp 200 may be a removable clamp configured to secure a first portion 310 of the aseptic connector 300 to a second portion 320 of the aseptic connector 300. The clamp 200 may include a number of components. For example, the clamp 200 may include a housing 222. The housing 222 may be formed of any suitable material, such as plastic. The housing 222 may be formed of one or more pieces that may be coupled together using, for example, screws, friction fit or snap fit components, and the like.

The clamp 200 may include one or more electronic components disposed within the housing 222. For example, the clamp 200 may include a controller disposed within the housing 222. The controller may be configured to control operation of one or more components of the clamp 200. The clamp 200 may include a rechargeable battery 240 disposed within the housing 222. The rechargeable battery 240 may be an internal battery and may or may not be externally accessible. For example, in some embodiments, the rechargeable battery 240 may be charged using inductive charging, in which case the battery may not be physically accessible by components external to the housing 222. The rechargeable battery 240 may be any suitable battery type, such as a coin cell battery, a lithium-ion battery, a nickel-cadmium battery, and/or a different type of battery. The rechargeable battery 240 may be configured for inductive charging. The rechargeable battery 240 may be configured to power one or more electronic components within or in communication with the clamp, such as the controller, a wireless radio, a sensor 360 of the aseptic connector 300, and/or other components.

The clamp 200 may include a wireless transmission device, such as a wireless radio 260 disposed within the housing 222. The wireless radio 260 may be configured to transmit and/or receive data, such as data captured or otherwise determined by the sensor(s) 360 of the aseptic connector 300. The wireless radio 260 may be, in one example, a Bluetooth radio configured for wireless communication using Bluetooth protocol or a ZigBee radio configured for wireless communication using ZigBee protocol. The wireless radio 260 may be configured for any suitable wireless communication, such as infrared, short-range radio frequency (RF) communication, Bluetooth, Bluetooth Low Energy (BLE), Wi-Fi, Wi-Max, Global System for Mobile (GSM), General Packet Radio Service (GPRS), Code Division Multiple Access (CDMA), High-Speed Downlink Packet Access (HSDPA), and the like.

The clamp 200 may include a sensor plug receptacle 250 configured to receive a sensor plug 380 that is coupled to the sensor 360 of the aseptic connector 300. The sensor plug receptacle 250 may be any suitable male, female, or genderless receptacle that is configured to couple or connect to the sensor plug 380. Data may be transmitted from the sensor 360 to the controller and/or wireless radio 260 via a wired connection from the sensor 360 that may include an interface at the sensor plug receptacle 250.

The clamp 200 may include a pivotable arm 210 that is configured to pivot with respect to the housing 222. The pivotable arm 210 may pivot about a joint 224 and may form a substantially circular opening 226 when in a closed position 232. Other embodiments may include different forms of arm joints, such as sliding, twisting, two-piece configurations, and so forth.

The clamp 200 may include a securing mechanism 228 to secure one arm to another. The securing mechanism 228 in FIG. 2 is illustrated as a rotatable screw 230. The rotatable screw 230 may be configured to engage a portion 220 of the housing 222 in order to secure the pivotable arm 210 to the housing 222.

The aseptic connector 300 may include the first portion 310 and the second portion 320. The second portion 320 of the aseptic connector 300 may be a connector body. One or more sensors 360 may be disposed within the connector body. For example, the connector body may include a cylindrical portion 322, and the sensor 360 may be disposed within a portion of the cylindrical portion 322. Accordingly, the sensor 360 may measure parameters of fluid flowing through the cylindrical portion 322.

An interface 330 between the first portion 310 and the second portion 320 may be compressed when the clamp 200 is engaged in a closed position and is secured about the outer surfaces of the respective first portion 310 and the second portion 320 of the aseptic connector 300.

The first portion 310 of the aseptic connector 300 may be an insert portion 340 and may include a tip of reduced diameter 350 in some embodiments. Fluid may flow through the connector body or second portion 320 to the insert portion or the first portion 310 of the aseptic connector 300.

The sensor 360 may be removably coupled to the connector body and/or second portion 320. The sensor 360 may be a single use sensor, such that it may be replaced after a bioprocessing cycle and/or after a certain amount of time. The sensor 360 may be integrated into the aseptic connector 300. The sensor 360 may be detachable from the aseptic connector 300 in some embodiments. The sensor 360 and/or the aseptic connector 300 may be disposable. The sensor 360 may be one or more of a pressure sensor, a temperature sensor, a potential of hydrogen (pH) sensor, a conductivity sensor, a glucose sensor, a biomass sensor, a cell viability sensor, an oxygen sensor, a carbon-dioxide sensor, an ultraviolet (UV) sensor, a flow sensor, a foam sensor, or combinations thereof. In some embodiments, the sensor 360 may be one or more of: a pressure transducer, a temperature sensor, a flow meter sensor, or a conductivity sensor. In some embodiments, more than one sensor may be included at the aseptic connector 300.

The sensor 360 may be coupled to a wire 370 that terminates at a sensor plug 380. The sensor plug 380 may engage the sensor plug receptacle 250 of the clamp 200 and may be used to communicate sensor readings or sensor output to the electronic components of the clamp 200. The clamp 200 may receive the sensor output and may transmit the sensor output using the wireless radio 260. The sensor plug 380 may be detachable from the sensor plug receptacle 250.

FIG. 3B illustrates another embodiment of the aseptic connector 300 with a spool piece 390. As illustrated in FIG. 3B, the aseptic connector 300 may include the spool piece 390, which may be configured to provide an inlet and outlet of the same diameter. Accordingly, the aseptic connector 300 may be configured to allow for sensor placement at flexible locations. The aseptic connector 300 of FIG. 3B may include a coupling interface 394 that is the same as the first portion 310. In some embodiments, the coupling interface 394 may be the mirror image of the first portion 310. The spool piece 390 may optionally include a tube 392 or other structure extending from the coupling interface 394. The tube 392 may have the same diameter as the coupling interface 394 in some embodiments.

FIG. 4 is a schematic drawing of the clamp 200 of FIG. 2 and the aseptic connector 300 of FIG. 3A in accordance with one or more embodiments of the disclosure.

The clamp 200 may be configured to secure the insert portion or the first portion of the aseptic connector 300 to the connector body or the second portion of the aseptic connector 300. The sensor(s) of the aseptic connector 300 may be coupled to the controller of the clamp 200 via a wire that is coupled to the sensor and a sensor plug. The sensor plug may removably engage a sensor plug receptacle at the housing of the clamp 200. Data from the sensor of the aseptic connector 200 may therefore be communicated to the controller of the clamp 300. The data may be wirelessly transmitted by the clamp 200 using one or more wireless radios. The clamp 200 may include a rechargeable battery that powers not only components of the clamp, but the sensor of the aseptic connector as well.

Figure 5:
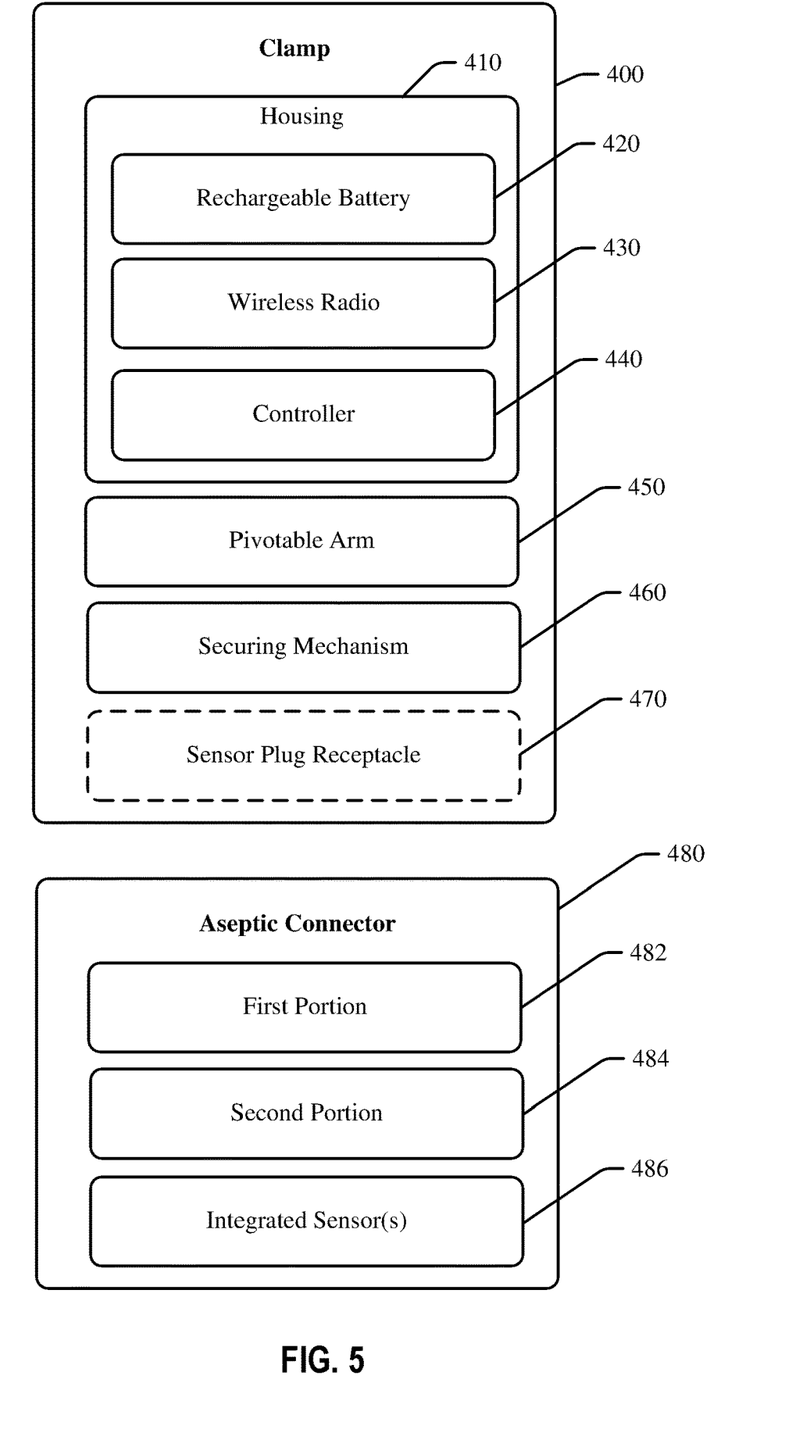
FIG. 5 is a schematic drawing of components of an aseptic connector system in accordance with one or more embodiments of the disclosure.

FIG. 5 is a schematic drawing of components of an aseptic connector system in accordance with one or more embodiments of the disclosure. The respective aseptic connector and/or clamp may be the same or different than the aseptic connectors and clamps previously discussed. Other embodiments may include connectors with additional or fewer, or different, components.

In FIG. 5, and example clamp 400 may include a housing 410. Disposed within the housing 410, the clamp 400 may include a rechargeable battery 420, a wireless radio 430, and a controller 440. The controller 440 may be configured to determine a sensor output of one or more integrated sensor (s) 486 of an aseptic connector 480, and may be configured to transmit the output using the wireless radio 430. For example, the controller 440 may be configured to wirelessly transmit sensor data or sensor output to a control system. The control system may receive the measured parameters of the fluid or other sensor output. In some embodiments, the controller 440 may be configured to transmit the data or sensor output over a local area network.

The clamp 400 may include a pivotable arm 450 or other mechanical component, a securing mechanism 460, such as a rotatable screw, and an optional sensor plug receptacle 470. In some embodiments, the controller 440 may be in wireless communication with the integrated sensor(s) 486, and the clamp 400 may therefore not include the sensor plug receptacle 470.

The aseptic connector 480 may include a first portion 482, which may be an insert portion, a second portion 484, which may be a connector body, and one or more integrated sensors 486.

Figure 6:
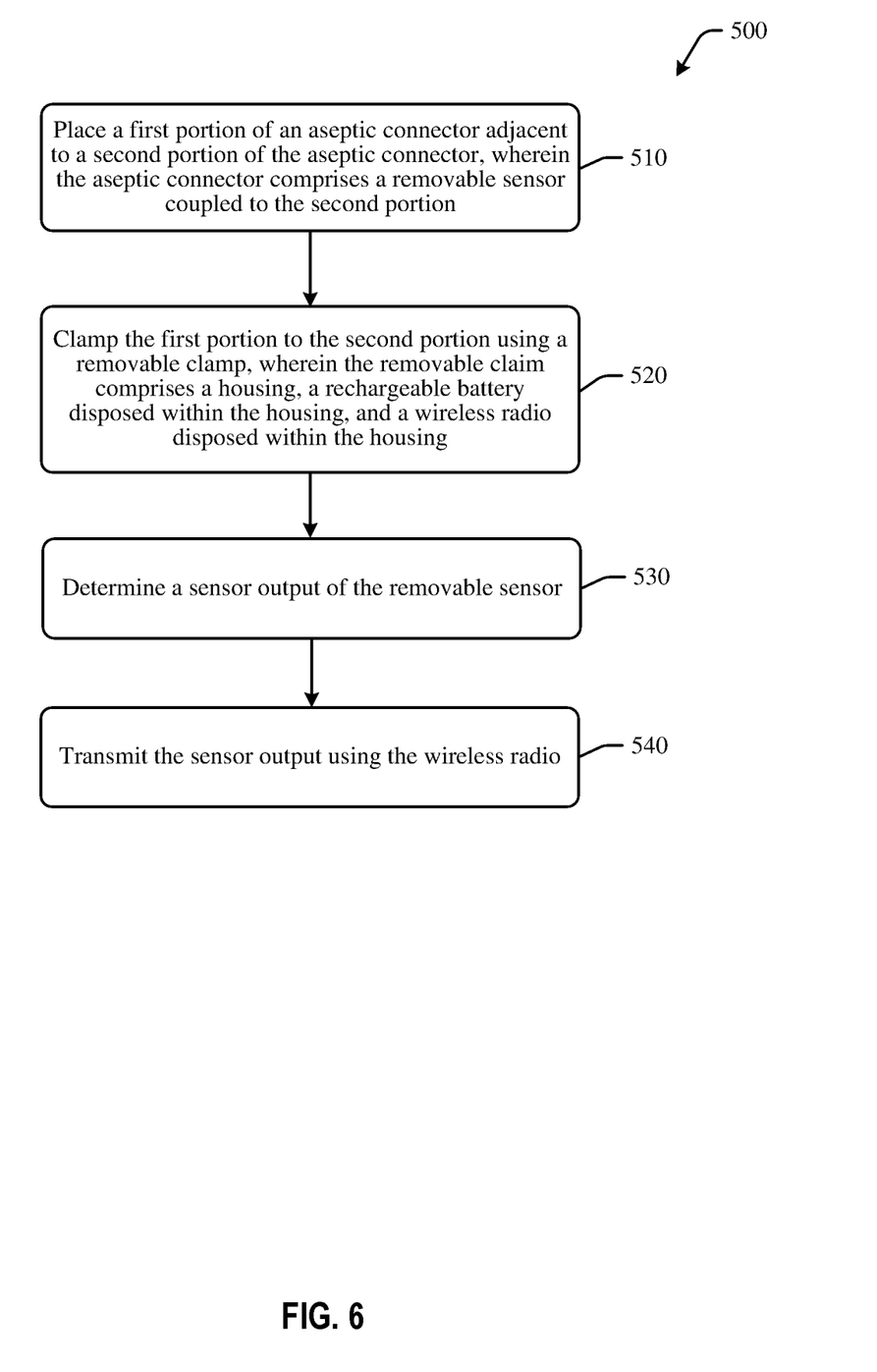
FIG. 6 is a schematic drawing of an example method of using an aseptic connector system in accordance with one or more embodiments of the disclosure.

FIG. 6 is a schematic drawing of an example method 500 of using an aseptic connector system in accordance with one or more embodiments of the disclosure. Other embodiments may include methods with additional or fewer, or different, operations. The operations illustrated in the example A first operation 510 includes placing a first portion of an aseptic connector adjacent to a second portion of the aseptic connector, wherein the aseptic connector comprises a removable sensor coupled to the second portion. For example, an insert portion may be placed adjacent to a connector body of an aseptic connector. The sensor may be removably coupled to the connector body. In some embodiments, the aseptic connector and/or sensor may be disposable and/or single use.

A second operation 520 may include clamping the first portion to the second portion using a removable clamp, wherein the removable claim comprises a housing, a rechargeable battery disposed within the housing, and a wireless radio disposed within the housing. For example, a removable clamp may be positioned about the aseptic connector, so as to secure the first portion to the second portion in a sterile manner while creating an airtight seal.

A third operation 530 may include determining a sensor output of the removable sensor. For example, the sensor may be powered by the rechargeable battery and may be configured to determine one or more fluid parameters or other readings.

A fourth operation 540 may include transmitting the sensor output using the wireless radio. For example, a controller at the clamp may receive the sensor output and may send the captured data, or at least a portion of the captured data, to, for example, a control system for monitoring of the bioprocess. One or more adjustments to the bioprocess may be implemented as a result of the output.

The various embodiments of the system and method aid in reducing clutter and improving efficiency in a bioprocess environment. By removing wires and assembly complexity, performance and efficiency may be improved, overall footprint size may be reduced, and cluttering may be reduced.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

That which is claimed is:

1. A system comprising:
a removable clamp configured to secure a first portion of an aseptic connector to a second portion of the aseptic connector, the removable clamp comprising:
a housing;
a controller disposed within the housing;
a rechargeable battery disposed within the housing;
a wireless radio disposed within the housing; and
a sensor plug receptacle configured to receive a sensor plug coupled to a sensor of the aseptic connector;
wherein the controller is configured to determine a sensor output of the sensor and to transmit the output using the wireless radio.

2. The system of claim 1, further comprising the aseptic connector, wherein second portion of the aseptic connector is a connector body, and wherein the sensor is disposed within the connector body.

3. The system of claim 2, wherein the first portion of the aseptic connector is an insert portion, and wherein a fluid flows through the connector body to the insert portion.

4. The system of claim 2, wherein the sensor is a single use integrated sensor.

5. The system of claim 2, wherein the sensor is removably coupled to the connector body.

6. The system of claim 2, wherein the sensor plug is configured to detach from the sensor plug receptacle.

7. The system of claim 1, wherein the removable clamp further comprises a pivotable arm that is configured to pivot with respect to the housing.

8. The system of claim 7, wherein the removable clamp further comprises a rotatable screw to secure the pivotable arm to the housing.

9. The system of claim 1, wherein the rechargeable battery is configured to be inductively charged.

10. The system of claim 1, wherein the sensor is one or more of: a pressure transducer, a temperature sensor, a flow meter sensor, or a conductivity sensor.

11. The system of claim 1, wherein the rechargeable battery is configured to power the sensor, the controller, and the wireless radio.

12. The system of claim 1, wherein the wireless radio is a Bluetooth radio or a ZigBee radio.

13. The system of claim 1, wherein the sensor is a first sensor, and wherein the system further comprises a second sensor at the aseptic connector.

14. The system of claim 1, wherein the controller is configured to transmit the output over a local area network.

15. A method comprising:
placing a first portion of an aseptic connector adjacent to a second portion of the aseptic connector, wherein the aseptic connector comprises a removable sensor coupled to the second portion;
clamping the first portion to the second portion using a removable clamp, wherein the removable claim comprises a housing, a rechargeable battery disposed within the housing, and a wireless radio disposed within the housing;
determining a sensor output of the removable sensor; and
transmitting the sensor output using the wireless radio.

16. An aseptic connector clamp system comprising:
an aseptic connector comprising:
an insert portion;
a connector body;
an integrated sensor coupled to the connector body, the integrated sensor coupled to a sensor plug;
a removable clamp configured to secure the insert portion to the connector body, the removable clamp comprising:
a housing;
a controller disposed within the housing;
a rechargeable battery disposed within the housing;
a wireless radio disposed within the housing; and
a sensor plug receptacle configured to receive the sensor plug.

17. The aseptic connector clamp system of claim 16, wherein the controller is configured to determine a sensor output of the integrated sensor and to transmit the output using the wireless radio.

18. The aseptic connector clamp system of claim 16, wherein the rechargeable battery is configured to be inductively charged.

19. The aseptic connector clamp system of claim 16, wherein the wireless radio is a Bluetooth radio or a ZigBee radio.

20. The aseptic connector clamp system of claim 16, wherein the aseptic connector is disposable.

* * * * *